United States Patent [19]

Eckenhoff

[11] Patent Number: 4,675,174

[45] Date of Patent: * Jun. 23, 1987

[54] VETERINARY DISPENSER DELIVERING BENEFICIAL AGENT BY GAS POWER GENERATED IN SITU

[75] Inventor: James B. Eckenhoff, Los Altos, Calif.

[73] Assignee: Alza Corporation, Palo Alto, Calif.

[ * ] Notice: The portion of the term of this patent subsequent to Jun. 17, 2003 has been disclaimed.

[21] Appl. No.: 766,372

[22] Filed: Aug. 16, 1985

[51] Int. Cl.⁴ .................. A61K 9/22; A61M 31/00
[52] U.S. Cl. ................................ 424/15; 424/467; 424/473; 604/890; 604/892
[58] Field of Search ............ 604/890, 892; 424/14, 424/15, 19

[56] References Cited

U.S. PATENT DOCUMENTS

| | | | |
|---|---|---|---|
| 2,340,037 | 1/1944 | Zipper | 424/37 |
| 3,732,865 | 5/1973 | Higuchi et al. | 604/892 |
| 3,760,804 | 9/1973 | Higuchi et al. | 604/892 |
| 3,760,805 | 9/1973 | Higuchi | 604/892 |
| 3,769,895 | 9/1973 | Higuchi | 354/292 |
| 3,845,770 | 11/1974 | Theeuwes et al. | 604/893 |
| 3,929,132 | 12/1975 | Higuchi | 604/892 |
| 3,995,632 | 12/1976 | Nakano et al. | 604/892 |
| 4,034,756 | 7/1976 | Higuchi et al. | 604/892 |
| 4,036,228 | 7/1977 | Theeuwes | 424/14 |
| 4,088,864 | 5/1978 | Theeuwes et al. | 219/121 |
| 4,178,361 | 12/1979 | Cohen et al. | 424/22 |
| 4,196,187 | 4/1980 | Dannelly et al. | 424/21 |
| 4,200,098 | 4/1980 | Ayer et al. | 604/892 |
| 4,203,441 | 5/1980 | Theeuwes | 424/14 |
| 4,235,236 | 11/1980 | Theeuwes | 604/892 |
| 4,265,874 | 5/1981 | Bonsen et al. | 424/15 |
| 4,285,987 | 8/1981 | Ayer et al. | 427/3 |
| 4,595,583 | 6/1986 | Eckenhoff et al. | 424/15 |

FOREIGN PATENT DOCUMENTS

| | | | |
|---|---|---|---|
| 449029 | 3/1972 | Australia | 424/14 |
| 2729068 | 11/1979 | Fed. Rep. of Germany . | |
| 1540258 | 9/1968 | France . | |

Primary Examiner—Ronald W. Griffin
Attorney, Agent, or Firm—Paul L. Sabatine; Edward L. Mandell; Steven F. Stone

[57] ABSTRACT

A dispensing system is disclosed for delivering a beneficial agent. The dispensing system comprises (1) a housing defining an internal space, (2) a gas-generating composition in the space, (3) a dense member in the space, (4) a composition comprising a beneficial agent and a non-toxic heat responsive carrier in the space, and (5) a passageway in the housing for delivering the beneficial agent for the dispensing system.

30 Claims, 8 Drawing Figures

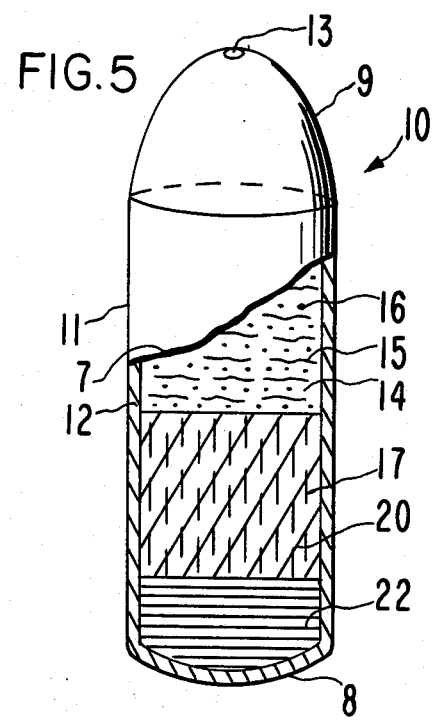
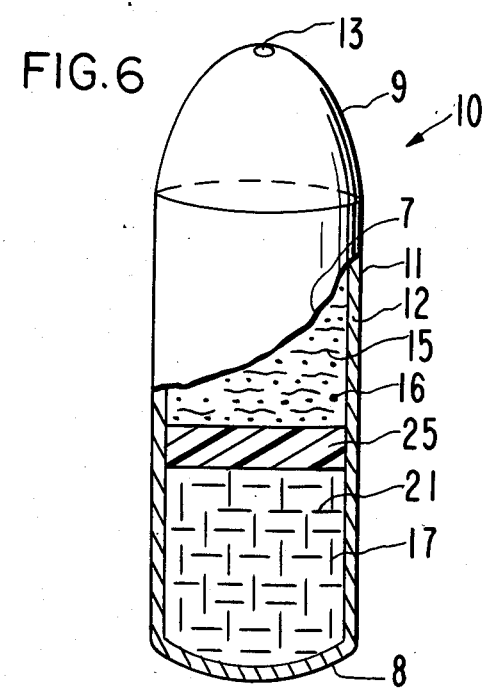
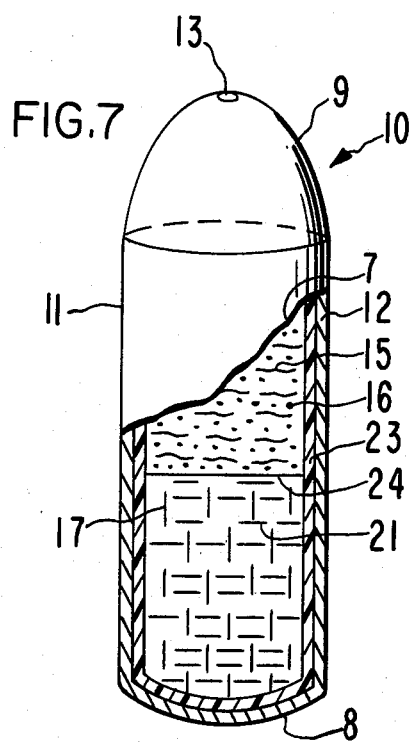
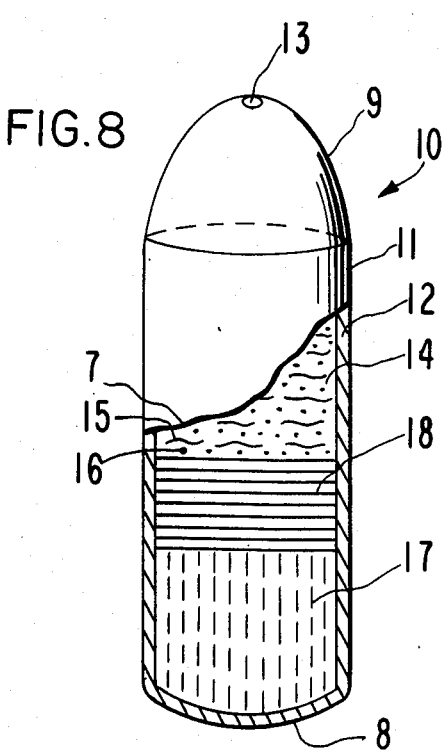

VETERINARY DISPENSER DELIVERING BENEFICIAL AGENT BY GAS POWER GENERATED IN SITU

FIELD OF INVENTION

This invention pertains to both a novel and useful dispenser. More particularly, this invention relates to an administrable dispenser which is orally administrable, and which dispenser delivers a controlled amount of a therapeutic agent, such as an anti-infectious agent, additive or nutrient agent when administered to a ruminant, into the reticulorumen of a ruminant over a prolonged period of time.

BACKGROUND OF THE INVENTION

It it well known that ruminant animals, including cattle, sheep, giraffe, deer, goat, bison and camels, and more specifically cattle and sheep, digest large quantities of feeds daily. These feeds are mostly cellulosic in content and they are swallowed with little chewing by the ruminant. The feeds are ingested into the largest of the four stomachs of the ruminant, called the rumen. The rumen is not a true stomach as it does not have any digestive glands. The rumen is somewhat in the nature of a storage compartment, and it is akin to a mixing organ containing a high concentration of bacteria. The bacteria in the rumen break up the cellulosic components present in the feed into simpler substances, which are more readily digestible by the ruminant. After this bacterial action upon the feed, it is regurgitated by the animal, masticated into finer particles, and re-swallowed by the animal. When the particles of feed are reduced further to a critical size, they pass from the rumen for further digestion in the true stomach of the animal.

The veterinary industry and veterinary medicine has long sought a dispenser that can release therapeutic agents, such as anti-infectious agents, feed additives and nutrient substances into the rumen in a controlled manner over a prolonged period of time. The dispenser is needed to maintain and improve the health of the animal, to fight off unwanted infections, to dispense feed additives that enhance feed efficiency, and to dispense nutrients that promote the growth of the animal. Often these beneficial agents must be given orally and they must be used in small quantities at frequent and regular intervals for their optimum benefits. These requirements make it difficult to administer these active agents properly for the management of the health and disease of the animal.

It is self-evident in view of the above presentation, a need exists for a dispenser that can dispense a beneficial agent in preselected amounts at a controlled rate over time. It is further self-evident a pressing need exists for an inexpensive, easy to manufacture dispenser that is especially adapted for dispensing a therapeutic agent, such as an anti-infectious agent, feed additive, or nutrient, into the reticulorumen of a ruminant in a preselected amount at a controlled rate over time.

OBJECTS OF THE INVENTION

Accordingly, it is a primary object of this invention to provide both a novel and useful dispenser for use in animal therapy, for promoting the growth of the animal and for maintaining the health of the animal, particularly a ruminant, and which dispenser fulfills the pressing need known to the prior art.

Another object of this invention is to provide a dispenser that is simple in construction and inexpensive to manufacture, which dispenser possesses all the practical benefits of long term controlled administration of various beneficial agents to animals, including warm-blooded animals such as ruminants.

Another object of this invention is to provide an improved dispenser that can store large amounts of beneficial agent and dispense the beneficial agent in small amounts over a prolonged period of time.

Another object of the invention is to provide a dispenser for administering to an animal, which dispenser houses a beneficial agent and protects it during storage, and which dispenser prevents leaching of the beneficial agent from the dispenser and a decrease in potency of the beneficial agent during its storage in the dispenser.

Another object of the invention is to provide a dispenser that contains a beneficial active agent in solid or semisolid form at room temperature, and which active agent is protected from the biological environment when the dispenser is in use, and which active agent becomes a dispensable paste or dispensable fluid at the body temperature of an animal.

Another object of the invention is to provide a sustained release dispenser that can remain in the rumenoreticular sac for an extended period and which dispenser exhibits a controlled sustained release pattern over this period.

Another object of this invention is to provide a dispenser which can administer a beneficial agent to a food producing ruminant for its intended effect.

Other objects, features, and advantages of this invention will be more apparent to those skilled in the medical and veterinary arts from the following detailed description of the specification, taken in conjunction with the drawing figures and the accompanying claims.

BRIEF DESCRIPTION OF THE DRAWINGS

In the drawing figures, which are not drawn to scale, but are set forth to illustrate various embodiments of the invention and not to be construed as limiting, the drawing figures are as follows:

FIG. 5 is an opened view of the dispenser of FIG. 1 for depicting the structure of the dispenser comprising a wall member, a thermo-responsive composition, a gas-generating couple and a density producing means;

FIG. 6 is an opened view of the veterinary dispenser of FIG. 1 for depicting the structure of the dispenser and the embodiment comprising a gas-impermeable member position between a thermo-responsive composition and a gas-generating couple;

FIG. 7 is an opened view of the dispenser of FIG. 1 depicting an embodiment wherein the dispenser comprises an inner and an outer wall in laminar arrangement and formed of different wall forming materials; and, FIG. 8 is an opened view of a dispenser comprising a density element of unit body shaped positioned between a beneficial agent formulation and a gas-generating means.

In the drawing figures and in the specification, like parts in related drawing figures are identified by like parts. The terms appearing earlier in the specification and in the detailed description of the drawing figures, as well as embodiments thereof, are detailed later in the disclosure.

DETAILED DESCRIPTION OF THE INVENTION

Figure 1:
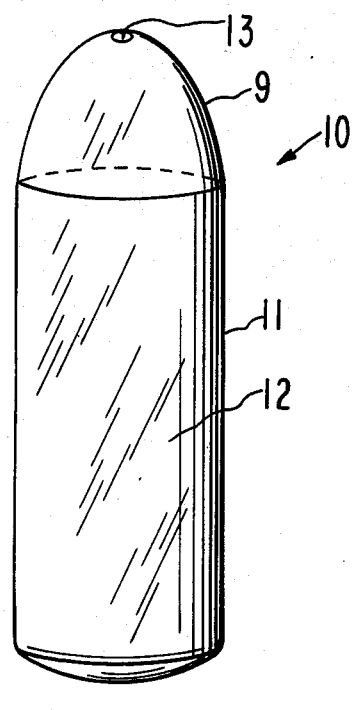
FIG. 1 is a view of a dispensing device designed and manufactured for orally administering a beneficial agent to a warm-blooded animal.

Turning now to the drawing figures in detail, which figures are examples of the novel and useful dispenser provided by the invention, and which examples are not to be construed as limiting, one example of a dispensing device is seen in FIG. 1, identified by the numeral 10. As seen in FIG. 1, dispenser 10 comprises a body 11 formed of a wall 12 that surrounds an internal chamber not seen in FIG. 1. Dispenser 10 comprises a passageway 13 for delivering a beneficial agent from dispenser 10. Dispenser 10 has a lead end 9 and rear end 8.

Figure 2:
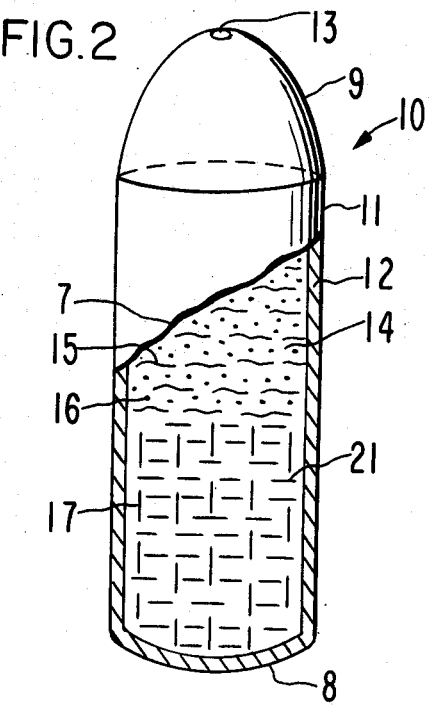
FIG. 2 is an opened view of the dispenser of FIG. 1 for depicting the structure of the dispenser comprising a wall member, a thermo-responsive composition, and a gas-generation couple comprising a density member homo geneously or heterogeneously blended therein.

FIG. 2 is an opened view of a dispenser 10 of FIG. 1, presently manufactured for veterinary use, with a section of wall 12 removed at 7. Dispenser 10 of FIG. 2 comprises body 11, wall 12, passageway 13, lead end 9 and rear end 8. Body 11 can embrace various shapes that are sized and adapted for oral admittance into an animal. The presently preferred shapes including tubular, cylindrical, and the like. Wall 12 surrounds and forms an internal compartment 14, which is an internal lumen. Wall 12 is formed in one presently preferred embodiment in at least a part of semipermeable wall-forming composition, or in another presently preferred embodiment wall 12 is formed completely of a semipermeable composition. The semipermeable composition is substantially permeable to the passages of an external fluid, and it is substantially impermeable to the passage of a beneficial agent and other ingredients contained in dispensing device 10. When wall 12 is formed in at least a part of a semipermeable composition, the rest of wall 12 is formed of a wall-forming composition that is substantially impermeable to the passage of fluid and it is substantially impermeable to the passage of beneficial agent and other ingredients housed in device 10. Wall 12 is, in either instance, formed of non-toxic materials, that maintains its physical and chemical integrity; that is, it does not erode or lose its integrity during the dispensing period. Compartment 14 contains a thermo-responsive, heat-sensitive composition 15, identified by wavy lines. Heat-sensitive composition 15 contains a beneficial agent formulation 16, identified by dots. Lumen 14 contains also a gas-generating means 17, identified by vertical dashes, which gas-generating member 17 is in contact with heat-sensitive composition 14. Gas-generating means 17 exhibits an osmotic pressure gradient across semipermeable wall 12 against an external fluid present in the environment of use. Gas-generating means 17 in a presently preferred embodiment comprises an effervescent couple and it is comprised of at least one acidic material and one basic material. Gas-generating means 17 in the presence of fluid imbibed through the semipermeable wall 12 into compartment 14 reacts in the presence of said imbibed fluid and generates gaseous pressure that is applied against thermo-responsive composition 15. This gaseous pressure against thermo-responsive composition 14 causes composition 15 to be delivered at a controlled rate through passageway 13 to the exterior of device 10 over 10. Compartment 14 of device 10 comprises further a density member 21, identified by horizontal dashes 21. Density member 21 is a densifier and is present in dispenser 10 for keeping dispenser 10 in the rumen of an animal during the beneficial agent dispensing period. Density member 21 in dispenser 10 is present homogeneously or heterogeneously mixed with gas-generating means 17, and density member is present in powder, particle, shot form or the like. Passageway 13 extends through semipermeable wall 12 for communicating the exterior of device 10 with lumen 14.

Figure 3:
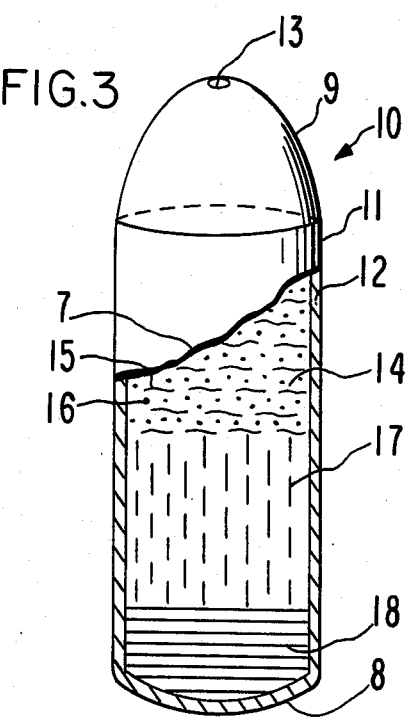
FIG. 3 is an opened view of the dispenser of FIG. 1, with FIG. 3 being similar to FIG. 2 with the added embodiment that the dispenser of FIG. 3 contains a weight member of unit body shape.

FIG. 3 depicts another manufacture provided by this invention. FIG. 3 is an opened view of dispensing device 10 of FIG. 1, and it comprises body member 11 having lead end 9, rear end 8, semipermeable wall 12 which is cut away at 7, passageway 13, and internal compartment 14 containing thermo-responsive composition 15 having beneficial agent formulation 16 distributed therein, and gas-generating means 17. Compartment 14 contains also a dense means 18 or densifier in contact with gas-generating means 17. Dense means 18 is a solid unit density member positioned in lumen 14 distant from heat-sensitive composition 15. Dense means 18 is present for keeping dispenser 10 in the animal over a prolonged period of time. In an embodiment, density member 18 can be located in layered contact with heat-sensitive composition 15.

Figure 4:
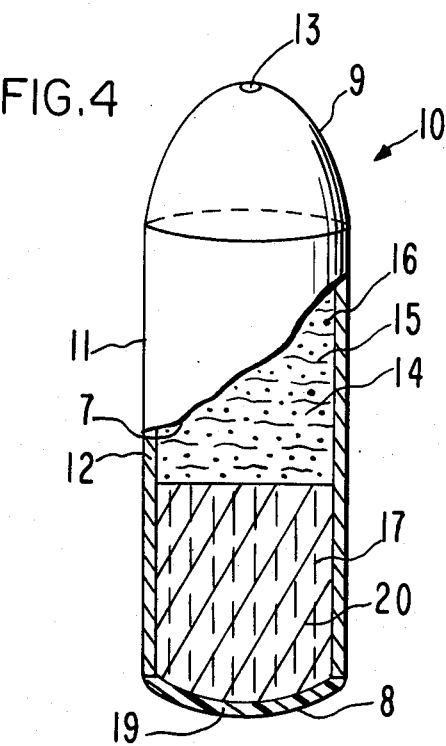
FIG. 4 is an opened view of the dispenser of FIG. 1 for depicting the structure of the dispenser comprising a wall member, a thermo-responsive composition and an expandable hydrogel containing a gas-generating couple.

FIG. 4 depicts another manufacture provided by the invention. FIG. 4 is an opened view of dispensing device 10 of FIG. 1, and it comprises body member 11 having lead end 9, rear end 8, and wall 12 surrounding compartment 14 and sectioned at 7. Wall 12 in FIG. 4 is formed of a wall-forming composition that is impermeable to both fluid and agent, except for a part of wall 12 at section 19 that is formed of a wall-forming material that is permeable to the passage of fluid and impermeable to the passage of a beneficial agent. In FIG. 4, compartment 14 contains thermo-responsive composition 15 comprising beneficial agent 16 in laminar arrangement with a combination driving member 20, which driving member 20 comprises gas-generating means 17 dispersed heterogeneously or homogeneously in an expandable driving member 20. Thermo-responsive composition 15 and expandable driving member 20 possess a shape that corresponds to the internal shape of lumen 14. Driving member 20 operates by the combined operations of (1) gas-generating means 17 imbibing fluid through semipermeable wall 19 into compartment 14 causing gas-generating means 17 to generate gas, and (2) by expandable member 20 imbibing fluid through semipermeable wall 19 into compartment 14 causing expandable member 20 to expand and increase in size, whereby through the combined operation of gaseous pressure the expanding pressure beneficial composition 15 is urged through passageway 13 from device 10 over time.

FIG. 5 depicts another manufacture provided by the invention. FIG. 5 is an opened view of dispensing device 10 of FIG. 1, and it comprises body member 11 comprising lead end 9, rear end 8, wall 12 sectioned at 7, which wall 12 surrounds and defines internal compartment 14, and a passageway 13 at lead end 9. Compartment 14 contains thermo-responsive composition 15 having beneficial agent formulation 16 dispensed therein. Compartment 14 also contains a driving member 20 in laminar arrangement with thermo-responsive composition 15. Driving member 20 comprises a gas-generating means 17 contained in an expandable driving member 20 that is formed of a hydrogel material. Device 10 additionally contains a dense member 22 in layered contact with expandable member 20. Density member 22 is solid or a comprised solid and it imparts weight to device 10, thereby enabling device 10 to remain in the rumen of the animal during the dispensing period.

FIG. 6 illustrates another dispensing device 10 provided by the invention. FIG. 6 is an opened view of dispenser 10 with a section of wall 12 removed at 7. Dispenser 10 comprises the structural members set forth for dispenser 10 in FIGS. 1 through 5, and in addition, dispenser 10 of FIG. 6 houses a diaphragm 25 positional between thermo-responsive composition 15 and gas generator 17. Diaphragm 25 is made of a material that is impermeable to the passage of gas or it exhibits low permeability to the passage of gas. The presence of diaphragm 25 assures that dispenser 10 becomes pressurized by lessening the incidence of gas loss from dispenser 10. The presence of diaphragm 25 in aiding in pressuring device 10 causes internal pressure to be directly applied against thermo-responsive composition 15, thereby exerting the force to discharge a metered formulation from dispenser 10.

FIG. 7 is an opened view of another dispenser 10 provided by the invention. Dispensing device 10 of FIG. 7 is similar to device 10 of FIGS. 1 through 6, with the added embodiment that in FIG. 7, dispenser 10 houses an internal capsule 23. Internal capsule is in laminar arrangement with outer wall 12. Internal capsule 23 surrounds compartment 14. The internal capsule 23 forms an inner wall surrounded by outer semipermeable wall 12. The internal capsule can comprise a single unit capsule body member, or it can be a dual body membered capsule. Passageway 13 extends through outer semipermeable wall 12 and inner capsule wall 23 for delivering the thermo-responsive beneficial composition to the exterior of dispenser 10.

FIG. 8 in another device provided by the invention wherein the device houses a density element 18 of singular construction positioned between a beneficial agent formulation 15 and a gas-generating formulation 17.

Dispensing device 10 of FIGS. 1 through 8 in operation in a biological environment of use, delivers beneficial agent composition 15 by a combination of thermodynamic and kinetic integrally performed activities. That is, in operation heat-sensitive composition, in response to the temperature of the environment, absorbs thermal energy and forms a deliverable composition, for example, a paste, semipaste, or fluid dispensable composition for delivering through passageway 13. As composition 15 melts and becomes flowable, external fluid concomitantly passed through semipermeable wall 12 into compartment 14. The fluid contacts gas-generating means 17 causing it to react and generate gas and gaseous pressure that is applied against melted composition 15. As more gas is generated, it occupies more volume in compartment 14, thereby urging composition 15 from device 10. Gas-generating means in one embodiment generates gas and forms an immiscible boundary at interface 24 as seen in FIG. 7. Device 10 is maintained in the biological environment, that is a rumen, by the presence of a dense member that is mixed with the gas-generating means or present as a separate element in device 10.

The dispensing device 10 can be manufactured in a variety of sizes and shapes for administering device 10 to ruminant animals. One presently preferred shape is a cylinder-like or capsule-like shape. For example, for use with sheep, dispensing device 10 can embrace a capsule-like shape and have a diameter of about 0.5 inches to 1 inch (1.3 cm to 2.5 cm) and a length of about 0.5 inches to about 1 inch (1.3 cm to 6.6 cm). For use with cattle, device 10 has a diameter of about 0.5 inches to 1.5 inches (1.3 cm to 3.8 cm), and a length of about 1 inch to 3.5 inches (2.5 cm to 7.8 cm). While FIGS. 1 through 8, illustrate various dispensing devices 10 that can be made according to the invention, it is to be understood these devices are not to be construed as limiting the invention, as the dispenser can take other shapes, sizes and forms for delivering beneficial agents to the biological environment of use. The dispensing device can be used in veterinary clinics, farms, zoos, laboratories, on the range, in feed lots, and other environments of use.

DETAILED DESCRIPTION OF THE INVENTION

In accordance with the practice of this invention, it has now been found representative materials for forming a wall 12 include semipermeable homopolymers, semipermeable copolymers, and the like. In one embodiment typical materials include cellulose esters, cellulose monoesters, cellulose diesters, cellulose triesters, cellulose ethers, cellulose ester-ethers, mixtures thereof, and the like. These cellulosic polymers have a degree of substitution, D.S., on their anhydroglucose unit from greater than 0 up to 3 inclusive. By degree of substitution is meant the average number of hydroxyl groups originally present on the anhydroglucose unit that are replaced by a substituting group, or converted into another group. The anhydroglucose unit can be partially or completely substituted with groups such as acyl, alkanoyl, aroyl, alkyl, alkenyl, alkoxy, halogen, carboalkyl, alkylcarbamate, alkylcarbonate, alkylsulfonate, alkylsulfamate, and like semipermeable polymer forming groups. The semipermeable materials typically include a member selected from the group consisting of cellulose acylate, cellulose diacylate, cellulose triacylate, cellulose acetate, cellulose diacetate, cellulose triacetate, mono-, di- and tri-cellulose alkanylates, mono-, di- and tri-cellulose alkanylates, mono-, di- and tri-alkenylates, mono-, di- and tri-aroylates, and the like. Exemplary polymers including cellulose acetate having a D.S. of 1.8 to 2.3 and an acetyl content of 32 to 39.9%; cellulose diacetate having a D.S. of 1 to 2 and an acetyl content of 21 to 35%; cellulose triacetate having a D.S. of 2 to 3 and an acetyl content of 34 to 44.8%, and the like. More specific cellulosic polymers include cellulose acetate propionate having an acetyl content of 1.5 to 7% and an acetyl content of 2.5 to 3%, an average propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose acetate butyrate having an acetyl content of 2 to 29.5%; a butyryl content of 17 to 53%, and a hydroxyl content of 0.5 to 4.7%; cellulose triacylates having a D.S. of 2.9 to 3 such as cellulose trivalerate, cellulose trilaurate, cellulose trilaurate, cellulose tripalmitate, cellulose trioctanoate, and cellulose tripropionate; cellulose diesters having a D.S. of 2.2 to 2.6 such as cellulose disuccinate, cellulose dipalmitate, cellulose dioctanoate, cellulose dicarpylate; cellulose propionate morpholinobutyrate; cellulose acetate butyrate; cellulose acetate phthalate; and the like; mixed cellulose esters such as cellulose acetate valerate, cellulose acetate succinate, cellulose succinate, cellulose acetate octanoate, cellulose valerate palmitate, cellulose acetate heptonate, and the like. Semipermeable polymers are known in U.S. Pat. No. 4,077,407, and they can be made by procedures described in *Encyclopedia of Polymer Science and Technology*, Vol. 3, pp 325 to 354, 1964, published by Interscience Publishers, Inc., New York.

Additional semipermeable polymers include cellulose acetaldehyde dimethyl cellulose acetate; cellulose acetate ethylcarbamate; cellulose acetate methylcarbamate; cellulose dimethylaminoacetate; a cellulose composition comprising cellulose acetate and hydroxypropyl methylcellulose; a composition comprising cellulose acetate and cellulose acetate butyrate; a cellulose composition comprising cellulose acetate butyrate and hydroxyPropyl methylcellulose; semipermeable polyamides; semipermeable polyurethanes; semipermeable polysulfones; semipermeable sulfonated polystyrenes, crosslinked, selectively semipermeable polymers formed by the coprecipitation of a polyanion and a polycation as disclosed in U.S. Pat. Nos. 3,173,876; 3,276,586, 3,541,005; 3,541,006, and 3,546,142; selectively semipermeable silicon rubbers; semipermeable polymers as disclosed by Loeb and Sourirajan in U.S. Pat. No. 3,133,132; semipermeable polystyrene derivatives; semipermeable (polysodium-styrenesulfonate); semipermeable poly(vinylbenzyltrimethyl) ammonium chloride, semipermeable polymer exhibiting a fluid permeability of $10^{-1}$ to $10^{-7}$ (cc. mil/cm$^2$hr. atm) expressed as per atmosphere of hydrostatic or osmotic pressure difference across a semipermeable wall. The polymers are known to the art in U.S. Pat. Nos. 3,845,770; 3,916,899, and 4,160,020, and in *Handbook of Common Polymers*, by Scott, J. R. and Roff, W. J., 1971, published by CRC Press, Cleveland, Ohio.

Wall 12 also can comprise a flux regulating agent. The flux regulating agent is a compound added to a wall forming composition for assisting in regulating the fluid permeability of flux through the wall. The flux regulating agent can be a flux enhancing agent or a flux decreasing agent. The agent can be preselected to increase or decrease the liquid flux. Agents that produce a marked increase in permeability to fluid such as water, are often essential hydrophilic, while those that produce a marked decrease to fluids such as water, are essentially hydrophobic. The amount of regulator in the wall when incorporated therein generally is from about 0.01% to 20% by weight or more. The flux regulator agents in one embodiment that increase flux include polyhydric alcohols, polyalkylene glycols, polyalkylenediols, polyesters of alkylene glycols, and the like. Typical flux enhancers include polyethylene glycol 300, 400, 600, 1500, 4000, 6000 and the like; low molecular weight glycols such as polypropylene glycol, polybutylene glycol and polyamylene glycol; the polyalkylenediols such as poly(1,3-propanediol), poly(1,4-butanediol), poly(1,6-hexanediol), and the like; aliphatic diols such as 1,3-gutylene glycol, 1,4-pentamethylene glycol, 1,4-hexamethylene glycol, and the like; alkylene triols such as glycerine, 1,2,3-butanetriol, 1,2,4-hexanetriol, 1,3,6-hexanetriol and the like; ester such as ethylene glycol diproprionate, ethylene glycol butyrate, butylene glycol diproprionate, glycerol acetate esters, and the like. Representative flux decreasing agents include phthalates substituted with an alkyl, an alkoxy or with both an alkyl and alkoxy group such as diethyl phthalate, dimethoxyethyl phthalate, dimethyl phthalate, and [di(2-ethyl-hexyl) phthalate]; aryl phthalates such as triphenyl phthalate, and butyl benzyl phthalate; insoluble salts such as calcium sulphate, barium sulphate, calcium phosphate, and the like; insoluble oxides such as titanium oxide; polymers in powder, granule and like form such as polystyrene, polymethylmethacrylate, polycarbonate, and polysulfone; esters such as citric acid esters esterified with long chain alkyl groups; inert and substantially water impermeable fillers; resins compatible with cellulose based wall forming materials, and the like.

Other materials that can be used to impart flexibility and elongation properties to the semipermeable wall, for making the semipermeable wall less brittle, and for increasing the tear strength include plasticizers presently exemplified by phthalate plasticizers such as dibenzyl phthalate, dihexyl phthalate, butyl octyl phthalate, straight chain phthalates of six to eleven carbons, diisononyl phthalate, diisodecyl phthalate, and the like. The plasticizers include nonphthalates such as triacetin, dioctyl azelate, epoxidized tallate, triisoctyl trimellitate, triisononyl trimellitate, sucrose acetate isobutyrate, epoxidized soybean oil, and the like. The amount of plasticizer in a wall when incorporated therein is about 0.01% to 20% by weight, or higher.

In the embodiment wherein wall 12 is formed in at least a part of a semipermeable polymeric composition, the rest of wall 12 can be formed of a material that is substantially impermeable to the passages of an external fluid. For example, stainless steel, low carbon steel coated with an alloy or metal, nylon, poly(ethylene terephthalate), poly(hexamethylene adipamide), poly(tetrafluoroethylene), poly(chlorotrifluoroethylene), poly(ethylene tetrasulphide), poly(vinylidene chloride), poly(vinylidene fluoride), and the like.

In the embodiment wherein dispenser 10 comprises an inner positional capsule contacted by an outer wall, the capsule member generically is tubular shaped and it has a mouth at one end, and at the end distant therefrom it is closed in a hemispherical or dome shaped end. The capsule member serves as a hollow body having a wall that surrounds and defines an interior compartment provided with an opening for establishing communication with the exterior of the capsule and for filling the capsule. In one manufacture, a capsule is made by dipping a mandrel, such as a stainless-steel mandrel, into a bath containing a solution of a capsule wall forming material to coat the mandrel with the material. Then, the mandrel is withdrawn, cooled, and dried in a current of air. The capsule is stripped from the mandrell and trimmed to yield a capsule with an internal lumen. The materials used for forming the capsule are commercially available materials including gelatin, gelatin having a viscosity of 15 to 30 millipoises and a bloom strength up to 150 grams; gelatin having a bloom value of 160 to 250; a composition comprising gelatin, glycerine water and titanium dioxide; a composition comprising gelatin, erthrosine, iron oxide and titanium oxide; a composition comprising gelatin, glycerine, sorbitol, potassium sorbate and titanium dioxide; a composition comprising gelatin, acacia, glycerin and water; water soluble polymers that permit the transport of water therethrough and can be made into capsules, and the like.

Exemplary materials suitable for forming diaphragm 22 that serves as a partition separating the thermo-responsive composition from the gas-generating means include polymer films that are substantially impermeable to the passage of a gas, or exhibiting a low permeability to the passage of gas, more specifically carbon dioxide. Polymeric films suitable for the present purpose include poly(vinyl butyral), poly(vinyl trifluoroacetate), poly(terephalic ester), neoprene, polystyrene, butadiene rubber, methyl rubber, Buna S, and the like. The permeation of a gas through a polymer film is primarily a diffusion-controlled process. Procedures and a permeability cell useful for ascertaining the permeability of films are described in *Ind. Eng. Chem.*, Vol. 48, pp 821–824, 1956; *Ind. Eng. Chem.*, Vol. 49, pp 1933–1936, 1957; and in *J. Appl. Phys.*, Vol. 17, pp 972–985, 1946.

Gas-generating means 17 suitable for the purpose for the invention in one presently preferred embodiment comprises an effervescent couple. The gas-generating means comprises at least one preferably solid acidic material and at least one preferably solid basic material. The acidic material and the basic material imbibe fluid into dispenser 10, dissolve and react, in the imbibed aqueous fluid, to produce carbon dioxide gas. This continuously fills the rear of the dispenser and by gas pressure and volume displacement dispenses beneficial agent from the dispenser. The acidic material and the basic material are present in the compartment in powder, crystalline, granular, pellet, or layered form. The acid that can be used include organic acids such as fumaric, tartaric, itaconic, maleic, citric, adipic, succinic and mesaconic, mixtures thereof, and the corresponding anhydrides such as itaconic anhydride, citriconic anhydride, and the like. Also, inorganic acids can be used such as sulfamic or phosphoric, and the acid disclosed in U.S. Pat. No. 3,325,357. Acid salts can be used, such as monosodium citrate, potassium acid tartrate, and potassium bitartrate. The gas-generating basic compounds include a member selected from the group consisting of carbonate and bicarbonate salts such as alkali metal carbonates and bicarbonates, or alkaline earth carbonates and bicarbonates and mixtures thereof. Exemplary materials include the alkali metals lithium sodium and potassium carbonate and bicarbonate, and the alkaline earth compounds magnesium and calcium carbonate or bicarbonate. Also useful are ammonium carbonate, ammonium bicarbonate, and ammonium sesquicarbonate. A combination of certain of these acid and base compounds results in a more rapid gas production over time. For example, either citric acid or a mixture of citric acid and tartaric acid and sodium bicarbonate are useful for the intended purpose. The initially essentially anhydrous or dry gas generating means is preferred, preferably present in substantially stoichiometrically balance to produce a combination that generates carbon dioxide. The acid and base materials can be used in any convenient proportion such as 1 to 200 parts and 200 to 1 part on a weight basis to produce the desired results.

A weight means, or density increasing member, also referred to as densifier, that can be used for the present purpose is homogeneously or heterogeneously blended with the gas-generating means. The weight means is used for initially retaining device 10 in the rumen-reticular sac of a ruminant. The dense member lets device 10 remain in the rumen during the dispensing period before device 10 passes into the alimentary tract and eliminated therefrom. During the period of time device 10 remains in the rumen, beneficial active agent is delivered by device 10 at a controlled rate to the ruminant over time. Generally, the amount of weight means mixed with the gas-generating means will be an amount sufficient to impart an initial density to the dispenser of from greater than 1 to 8, with the density in a presently preferred embodiment exhibiting a specific gravity of from 2.2 to 7.6. For ruminant cattle and sheep, it is presently preferred the combination gas-generating means and weight means initially exhibit a density such that there is a resulting system density of about 3. Materials that have a density greater than 1 to 8 that can be blended with the gas-generating means include iron, iron shot, iron shot coated with iron oxide, iron shot magnesium alloy, steel, stainless steel, copper oxide, a mixture of cobalt oxide and iron powder, a mixture of iron and copper oxide, and the like. The weight means can be in powder, granule, pellet and like form for blending with the gas-generating means. The dense member additionally can be a solid member having a shape that corresponds to the internal shape of dispenser 10. The solid member can optionally have a bore extended therethrough for the passage of agents. The density member can be incorporated to remain within the dispenser for the lifetime of the ruminant comprising a unit body shape; or when blended with the driving member or with the beneficial agent in these embodiments to eventually cause the dispenser to pass from the alimentary tract after delivery of the beneficial agent.

The gas-generating means can be dispersed or blended with an expandable hydrogel for obtaining the combined benefits of gas pressure and expanding hydrogel pressure. The expandable means preferably has a shape that corresponds to the internal shape of compartment 14 and it is made from a hydrogel composition. The hydrogel composition is noncross-linked or optionally cross-linked and it possesses osmotic properties, such as the ability to imbibe an exterior fluid through the semipermeable wall, and it exhibits an osmotic pressure gradient across the semipermeable wall against a fluid outside dispensing device 10. The materials used for forming the swellable, expandable inner hydrogel for blending with the gas generator are polymeric materials that interact with water or biological fluid, absorb the fluid and swell or expand to an equilibrium state. The polymer exhibits the ability to retain a significant fraction of imbibed fluid in the polymer molecular structure. The polymers in a preferred embodiment are gel polymers that can swell or expand to a very high degree, usually exhibiting a 2 to 50 fold volume increase. The swellable, hydrophilic polymers, also and the osmopolymers can be noncross-linked or lightly cross-linked. The cross-links can be covalent or ionic bonds with the polymer possessing the ability to swell in the presence of fluid, and when cross-linked with non-mobile bonds, they will not dissolve in the presence of aqueous fluid. The polymer can be of plant, animal or synthetic origin. Polymeric materials useful for the present purpose include poly(hydroxyalkyl methacrylate) having a molecular weight of from 5,000 to 5,000,000; poly(vinylpyrrolidone) having a molecular weight of from 10,000 to 360,000; anionic and cationic expandable hydrogels; poly(electrolyte) complexes; poly(vinyl alcohol) having a low acetate residual; a swellable mixture of agar and carboxymethyl cellulose; a swellable composition comprising methyl cellulose mixed with a sparingly cross-linked agar; a water-swellable copolymer produced by a dispersion of finely divided copolymer of maleic anhydride with styrene, ethylene, propylene, or isobutylene; water swellable polymer of N-vinyl lactams, and the like.

Other hydrogel or gelable fluid absorbing and or imbibing and retaining polymers useful for forming hydrophilic, expandable push member include pectin having a molecular weight ranging from 30,000 to 300,000; polysaccharides such as agar, acacia, karaya, tragacanth, algins and guar; Carbopol ® acidic carboxy polymer and its salt derivatives; polyacrylamides; water-swellable indene maleic anhydride polymers; Goodrite ® polyacrylic acid having a molecular weight of 80,000 to 200,000; Polyox ® polyethylene oxide polymers having a molecular weight of 100,000 to 5,000,000; starch graft copolymers; Aqua-Keep ® acrylate polymers with water absorbability of about 400 times its original weight; diesters of polyglucan; a mixture of cross-linked polyvinyl alcohol and poly(N-vinyl-2-pyrrolidone); zein available as prolamine; poly(ethylene glycol) having a molecular weight of 4,000 to 100,000, and the like. In an embodiment, the expandable member is formed from polymers and polymeric compositions that are thermo-formable. The term "thermo-formable" indicates a standard process wherein the polymer is softened by heat, forced against a mold and assumes the shape of the mold. The word "thermo" denotes pertaining to heat. The gas-generating means can be blended with the hydrogel during polymerization, by blending solvent casting and evaporation, by comprising a blend and the like. The amount of weight means blended with a hydrogel is about 0.5 to 50 wt %, or an amount sufficient to produce the desired density. Density, specific gravity, and specific volume determinations are easily performed by procedures known in the art as disclosed in *Remington's Pharmaceutical Sciences*, Volume 14, pages 95 to 100, edited by Osol and published in 1970 by Mack Publishing Co., Easton, Pa. Representative polymers possessing hydrophilic properties are known in U.S. Pat. Nos. 3,865,108; 4,002,173; 4,207,893; 4,327,725, and in *Handbook of Common Polymers; by Scott and Roff, published by Cleveland Rubber Company, Cleveland, Ohio*.

The thermo-responsive composition containing a beneficial agent homogeneously or heterogeneously dispersed or dissolved therein, is formed, in a presently preferred embodiment, of a heat sensitive, hydrophobic material that exhibits solid-like properties at room temperature of 25° C., and within a few centigrade degrees thereof, and exhibits in a dispensable point at 25° C. to 45° C. The present invention uses the phrases "melting point", "softening point", "pour point", or "liquifies" to indicate the temperature at which the thermo-responsive composition melts, undergoes dissolution, or forms a paste-like ribbon, dissolves to form a dispensable carrier so it can be used for dispensing the beneficial agent from dispenser 10. The term, "thermo-responsive" as used for the purpose of this invention includes thermoplastic compositions capable of softening, melting, becoming extrudable, becoming fluid, or becoming dispensable in response to heat and hardening again when cooled. The term also includes thermotropic compositions capable of undergoing change and becoming dispensable in response to the application of energy in a gradient manner. These materials also are temperature sensitive in their response to the application, and to the withdrawal of energy. The term "thermo-responsive" as used for the purpose of this invention in a preferred embodiment denotes the physical-chemical property of a composition agent carrier to exhibit solid, or solid-like properties at temperatures up to 25° C., and become fluid, semisolid, or viscous when disturbed by heat at temperatures from 31° C., usually in the range of 25° C. to 45° C. The thermo-responsive carrier is heat-sensitive and preferably anhydrous and it has the property of melting, dissolving, undergoing dissolution, softening, or liquifying at the elevated temperatures, thereby making it possible for the dispenser 10 to deliver the thermo-responsive carrier with the beneficial agent homogeneously or heterogeneously blended therein. The thermo-responsive carrier can be lipophilic, or hydrophobic. Another important property of the carrier is its ability to maintain the stability of the agent contained therein during storage and during delivery of the agent.

Representative thermo-responsive compositions and their melting points are as follows: food grade petroleum waxes, 25° C. to 45° C.; cocoa butter 32°–34° C.; cocoa butter plus 2% beeswax 35°–37° C.; propylene glycol monostearate and distearate 32°–35° C.; hydrogenated oils such as hydrogenated vegetable oil 36°–37.5° C.; 80% hydrogenated vegetable oil and 20% sorbitan monopalmitate 39–39.5%., 80% hydrogenated vegetable oil and 20% polysorbate 60, 36°–37° C., 77.5% hydrogenated vegetable oil, 20% sorbitan trioleate and 2.5% beeswax 35°–36° C., 72.5% hydrogenated vegetable oil, 20% sorbitan trioleate, 2.5% beeswax and 5.0% distilled water, 37°–38° C.; mono-, di-, and triglycerides of acids having from 8–22 carbon atoms including saturated and unsaturated acids such as palmitic, stearic, oleic, lineolic, linolenic and archidonic; glycerides of fatty acids having a melting point of at least 32° C. such as monoglycerides, diglycerides and triglycerides of vegetable fatty acids having 10 to 18 carbon atoms obtained from coconut oil, olive oil and the like; partially hydrogenated cottonseed oil 35°–39° C.; hardened fatty alcohols and fats 33°–36° C.; hexadienol and hydrous lanolin triethanolamine glyceryl monostearate 38° C.; eutectic mixtures of mono-, di-, and triglycerides 35°–39° C.; Witepsol ® #15, triglyceride of saturated vegetable fatty acid with monoglycerides, 33.5°–35.5° C.; Witepsol ® H32 free of hydroxyl groups, 31°–33° C.; Witepsol ® W25 having a saponification value of 225–240 and a melting point of 33.5°–35.5° C.; Witepsol ® E75 having a saponification value of 220–230 and a melting point of 37°–39° C.; a polyalkylene glycol such as polyethylene glycol 1000, a linear polymer of ethylene oxide, 38°–41° C.; polyethylene glycol 1500, melting at 38°–41° C.; polyethylene glycol monostearate, 39°–42.5° C.; 33% polyethylene glycol 1500, 47% polyethylene glycol 6000 and 20% distilled water, 39°–41° C.; 30% polyethylene glycol 1500, 40% polyethylene glycol 4000 and 30% polyethylene glycol 400, 33°–38° C.; mixture of mono-, di-, and triglycerides of saturated fatty acids having 11 to 17 carbon atoms, 33°–35° C.; block polymer of 1,2-butylene oxide and ethylene oxide; block polymer of propylene oxide and ethylene oxide; block polymer of polyoxyalkylene and propylene glycol, and the like. The thermo-responsive composition is a means for storing a beneficial agent in a solid composition at a temperature up to 25° C., maintaining an immiscible boundary at the swelling composition interface, and for dispensing the agent in a flowable composition at a temperature greater than 25° C., and preferably in the range of 25°–45° C. The thermo-responsive composition on being dispensed into a biological environment are easily excreted, metabolized, assimilated, or the like, for effective use of the beneficial agent.

The term, "beneficial agent" as used herein includes medicines or drugs, nutrients, vitamins, anthelmintic, biocide, parasiticide, food supplements, and other agents that benefit a ruminant animal. The beneficial agent can be insoluble to very soluble in the temperature sensitive material housed in the delivery system. The amount of agent present in a delivery system can be from 10 ng to 40 g or more. The delivery system can house various amounts of the beneficial agent, for example, 75 ng, 1 mg, 5 mg, 100 mg, 250 mg, 750 mg, 1.5 mg, 2 g, 5 g, 10 g, 15 g, and the like. A single delivery system can be administered to a ruminant during a therapeutic program, for administering from 10 mg/hr to 1500 mg/hr of a beneficial agent.

Representative of beneficial agent that can be dispensed using the delivery system of this invention include anthelmintics such as mebendazole, levamisole, albendazole, cambendazole, fenbendazole, parbendazole, oxfendazole, oxybendazole, thiabendazole, tichlorfon, praziquantel, morantel and pirantel, and the like; antiparasitic agents such as avermectins and ivermectin, as disclosed in U.S. Pat. Nos. 4,199,569 and 4,389,397 both assigned to Merck & Co., and in *Science*, Vol. 221, pages 823 to 823, 1983, wherein said ivermectin antiparasitic drug are disclosed as useful for aiding in controlling commonly occurring infestations in animals, such as roundworms, lung worms and the like, and said ivermectin also being useful for the management of insect infestations such as grub, lice, mange mite, and the like; antimicrobial agents such as chlortetracycline, oxytetracycline, tetracycline, streptomycin, dihydrostreptomycin, bacitracins, erythromycin, ampicillins, penicillins, cephalosporins, and the like; sulfa drugs such as sulfamethazine, sulfathiazole, and the like; growth-stimulants such as Monesin ® sodium and Elfazepam ®; defleaing agents such as dexamethazone and flumethazone; rumen fermentation manipulators and ionophores such as lasalocid, virginamycin and ronnel; minerals and mineral salts; anti-bloat agents such as organopoly siloxanes; hormone growth supplements such as stilbestrol; vitamins; antienteritis agents such as furazolidone, nutritional supplements such as lysine monohydrochloride, methionine, magnesium carbonate; and the like.

The wall forming composition can be applied to from the device and as the exterior surface of the capsule in laminar arrangement by molding, air spraying, dipping, casting, or brushing, with a semipermeable wall forming composition. Other and presently preferred techniques that can be used for applying the wall are the air suspension procedure and the pan coating procedures. The air procedure consists in suspending and tumbling the compress arrangement of the device forming components in a current of air and a wall forming composition until the wall surrounds and coats the components or surrounds and coats the capsule member. The procedure can be repeated with a different wall forming composition to form a semipermeable laminated wall. The air suspension procedure is described in U.S. Pat. No. 2,799,241; *J. Am. Pharm. Assoc.*, Vol. 48, pages 451 to 459, 1979; and *ibid.*, Vol. 49, pages 82 to 84, 1960. Other standard manufacturing procedures are described in *Modern Plastics Encyclopedia*, Vol. 46, pages 62 to 70, 1969; and in *Pharmaceutical Sciences*, by Remington, 14th Edition, pages 1626 to 1678, 1970, published by Mack Publishing Co., Easton, Pa.

Exemplary solvents suitable for manufacturing the wall include inert inorganic and organic solvents that do not adversely harm the materials, the capsule wall, the beneficial agent, the thermo-responsive composition, the expandable member, the dense member, and the final dispenser. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, propylene dichloride, carbon tetrachloride, nitroethane, nitropropane, tetrachloroethane, ethyl ether, isopropyl ether, cyclohexane, cyclo-octane, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol. Generally, for the present purpose the wall is applied at a temperature a few degrees less than the melting point of the thermo-responsive composition. Or, the thermoplastic composition can be loaded into the dispenser after applying the wall.

The expression, "passageway" or "orifice" as used herein comprises means and methods in the semipermeable wall or in a laminated wall suitable for releasing a beneficial agent formulation from the dispenser. The passageway can be formed by mechanical or laser drilling, or by eroding an erodible element in the wall, such as gelatin plug. The passageway can be drilled through the semipermeable wall only, or through the semipermeable wall capsule laminated wall. In these embodiments when the passageway is drilled only through the semipermeable wall, the passageway in the capsule wall is formed in the environment of use by bursting, eroding, dissolving, leaching, or the like, a passageway in the capsule wall. The passageway can be a porous polymer composition having at least one pore, or a microporous polymer composition having at least one micropore or more than one micropore that serves as more than one passageway suitably made a part of the wall of the delivery system. The passageway can be positioned in a preselected loci of the wall by visual inspection, by optical density scanning as the device travels through a laser machine, by orienting and following the device through the manufacturing steps, by photo detection and responding to the reflected wavelength emanating from a device, by magnetic orientation, and like standard manufactured procedures. A detailed description of some orifices and the preferred maximum and minimum dimensions for an orifice are disclosed in U.S. Pat. Nos. 3,845,770 and 3,916,899.

DESCRIPTION OF EXAMPLES OF THE INVENTION

The following examples are merely illustrative of the present invention and they should not be construed as limiting the scope of the invention in any way, as these examples and other equivalents thereof will become more apparent to those skilled in the art in the light of the present disclosure, the drawings and the accompanying claims.

EXAMPLE 1

A dispensing system for the controlled delivery of ivermectin is made as follows: first, 193 g of Butronic ® L-1 polyol, a block polymer formed by the polymerization of 1,2-butylene oxide to which ethylene oxide is added, as reported in *Cosmetics and Toiletries*, Vol. 97, pages 61 to 66, 1982, which polymer flows at a pour point of 39° C., is melted at 55° C. and then 13.98 g of ivermectin is added thereto using a high sheer ultrasonic mixer. The resulting mixture is placed in a vacuum oven at 55° C. and the pressure reduced to less than 10 mm of mercury. The ivermectin Butronic composition is allowed to remain in the vacuum for a period of about 10 minutes for removing entrapped air. Next, 4 g of the resulting thermoplastic drug formulation is poured through the open tail and into the lead end of a ½ oz. gelatin capsule. Then, gas-generating means comprising 2.4 g of anhydrous citric acid and 8.5 g of anhydrous sodium bicarbonate are homogeneously blended in powder form and then charged into the open end of the capsule making contact with the drug polyol thermo-responsive composition. Next, the capsule is coated in a pan coater with a rate controlling wall comprising 1.8 g of 91% cellulose acetate butyrate and 9% polyethylene glycol 400. The wall is coated from a 5% wt/wt solution in methylene chloride methanol 90:10 v/v solvent system. The wall-coated delivery systems then are dried at 30° C. for 24 hours. Next, the device is visually oriented and a 30 mil exit passageway is drilled through the semipermeable wall and the gelatin capsule using a high speed mechanical drill for communicating the passageway with the internal compartment of the device. The passageway establishes communication; with the heat-responsive drug formulation for delivering it from the delivery system. The dispenser made according to this example releases the beneficial agent over a prolonged period of time.

EXAMPLE 2

The procedure of Example 1 is followed with all conditions as previously set forth. In the present example, the anhydrous citric acid and the anhydrous sodium bicarbonate are blended with 30 g of iron chips and the blended ingredients pressed into a solid tablet shape. The tablet is formed using a 18.2 mm tableting dye and 3½ tons of tableting compression. The shape tablet corresponds to the internal shape of the capsule. The gas-generating density tablet is inserted into the capsule until contact is made with the drug thermo-responsive composition. The capsule is surrounded with an outer wall comprising 95% cellulose acetate having an acetyl content of 39.8% and 5% polyethylene glycol having a molecular weight of 3350. Then, a passageway is drilled oriented by photo detection guidance through the dual walls for communicating with the drug thermo-responsive composition.

EXAMPLE 3

A dispensing device for the controlled delivery of the veterinary agent ivermectin is prepared as follows: first, 193 g of Butronic ® L-1 poly, a commercially available block polymer prepared by the polymerization of 1,2-butylene oxide to which ethylene oxide is added, which polymerization is reported in *Cosmetics and Toiletries*, Vol. 97, pages 61 to 66, 1982. The polymer flows at a pour point of 39° C. The polymer is melted at 55° C. and then 14 g of ivermectin is added to the melt using a high sheer ultrasonic mixer. The resulting mixture is placed 55° C. and then 14 g of ivermectin is added to the melt using a high sheer ultrasonic mixer. The resulting mixture is placed in a vacuum oven at 55° C. and the pressure reduced to less than 10 mm of mercury. The ivermectin Butronic composition is allowed to remain in the vacuum for a period of about 10 minutes, for removing entrapped air. Next, 7.5 g of the resulting thermoplastic ivermectin thermo-responsive composition is charged into a gelatin capsule. Then, a gas-generating means is prepared by thoroughly blending 6.4 g of potassium carbonate, 2.5 g of citric acid and 4.9 g of the sodium salt of polyacrylic acid available as Carbopol ® 934-P. The gas-generating hydrogel means is compressed into shape adapted for placement inside the capsule in intimate contact with the thermo-responsive formulation.

Next, the capsule is surrounded with a wall forming composition comprising cellulose acetate having an acetyl content of 39.8% and polyethylene glycol 3350 as described above. A passageway is drilled through the wall for establishing communication with the heat-responsive drug formulation for delivering it to a rumen over a prolonged period of time.

EXAMPLE 4

A veterinary dispenser is made according to the procedures set forth above, with the conditions as set forth, except that in this example, the heat-responsive composition comprises 46.6 g of ivermectin and 200 g of polyethylene glycol 400 distearate, and the gas-generating means comprises 16 parts of anhydrous alcohol moistened citric acid added to 21 parts by weight of sodium bicarbonate formed into granules by kneading them together in a mixer, and 20% by weight of a 50:50 mixture of iron shot and cobalt oxide.

EXAMPLE 5

A veterinary dispenser is made according to the procedure set forth above, with the conditions as set forth, except that in this example the heat-responsive dispensable formulation comprises 46.6 g of ivermectin and 200 g of polyethylene glycol 400 distearate, and the gas-generating means comprises 70% by weight of poly(ethylene oxide) having a molecular weight of 3,000,000, 10% by weight of a gas-generating composition consisting essentially of 16 parts by weight of anhydrous citric acid to 21 parts by weight of anhydrous sodium bicarbonate, and 20% by weight of a 50:50 mixture of iron shot and cobalt oxide.

EXAMPLE 6

A dispenser is prepared as follows: first, the body section of a capsule is positioned with its mouth in an upright position and a layer of a gas-generating composition charged into the hemispherical end of the capsule. The layer's shape matches the internal shape of the capsule. The gas-generating composition comprises 5% by weight of stoichiometrically balanced amount of succinic acid and magnesium carbonate, 70% by weight of poly(ethylene oxide) having a molecular weight of 200,000 and 25% by weight of stainless steel particles to yield the volume displacement composition. The ingredients are blended in a commercial blender with heat for 20 minutes to yield a homogeneous composition. The heated composition is charged into the capsule forming a layer that occupies about ⅓ of the capsule.

Next, a heat-sensitive drug formulation comprising an eutectic mixture of 77% neutral fat having a melting point of 35°-37° C. and 19.5% paraffin having a melting point of 52° C. is heated and 3.5% levamisole is added thereto. Then, the heated mixture is cooled to about 40° C. and injected into the capsule in contacting relation with the volume displacement gas-generating layer, and the capsule allowed to cool to room temperature.

Then, a solution of cellulose acetate, 15 wt %, with an acetyl content of 39.8%, is prepared in a methylene chloride methanol solvent system and the capsule coated with a semipermeable wall. The wall is applied by dipping it into the coating solution for 15 times, first for a 5 second dip and then for 1 minute per dip, with an intervening 5 minute drying period. Following the dipping the delivery dispenser is dried at room temperature, 72° F., about 22° C., for 5 days. The procedure applies about a 2 mm thick semipermeable wall. A passageway positioned by photo detection is laser drilled through the semipermeable wall connecting the exterior of the dispenser with the heat sensitive drug formulation for releasing it at a controlled rate over time.

EXAMPLE 7

A dispensing system for delivering beneficial nutrients to warm-blooded ruminants is prepared as follows: first, a mold having a shape and configuration corresponding to the internal diameter and the hemispherical closed end of a capsule, is filled with a gas-generating composition comprising 30 parts of ethyleneglycol monomethacrylate containing 0.12 parts of ethyleneglycol dimethacrylate, 10 parts of a 0.13% solution of sodium disulfate in ethanol, 30 parts of iron powder and magnesium, and 30 parts of sodium bicarbonate and citric and adipic acids. The composition polymerizes at 30° C., and after 20 minutes following equilibrium to room temperature, and the solid layer is removed from the mold. The solid gas-generating layer then is inserted, through the mouth of the capsule into the hemispherical area of the capsule. Next, the capsule is filled with a melted composition comprising 2.5% L-lysine HCl, 1.5% DL-methionine, 21% glycergelatin and 75% theobromo oil, a glyceride of stearic acid, palmitic acid and lauric acid, to form, on cooling to room temperature, a thermo-responsive composition in laminar position with the gas-generating dense member. Next, the filled capsule is coated with a surrounding wall comprising cellulose acetate containing 10% polyethylene glycol 400. The semipermeable wall is applied in a pan type Hi-coater. The solvent used for forming the wall consists essentially of methylene chloride and methanol 95 parts by weight to 5 parts by weight. A 12 mil, 0.30 mm, thick wall of cellulose acetate butyrate is applied to the exterior surface of the capsule. Finally, a passageway is laser drilled through the semipermeable wall and the capsule wall communicating with the heat-responsive nutrient containing composition for its delivery to the environment of use.

EXAMPLE 8

A delivery device is made according to the procedure set forth in Example 1, with the conditions and the materials as set forth, except that in this example a varying wall thickness comprising cellulose acetate butyrate and poly(ethylene glycol) 400 is applied to the device. The thickness of the wall varies from 30 mil (0.76 mm) as the rear end in a uniform taper to 15 mil (0.38 mm) lead end.

EXAMPLE 9

A delivery device is prepared by following the procedure set forth above. The delivery device comprises a first compressed composition comprising 25 g of poly(ethylene oxide) having a molecular weight of 500,000, 25 g of iron powder, 10 g of citric acid and 10 g of potassium bicarbonate pressed against a second compressed composition comprising 38.5 g of neutral fat, 9.7 g of paraffin and 1.7 g of purbendazole. The laminated compressed layers as surrounded with a semipermeable wall that comprises 50% cellulose acetate butyrate, 45% poly(sulfone) and 5% citroflex citric acid ester selected form the group consisting of acetyl tributyl citrate and acetyl tri-2-ethylhexyl citrate. The delivery device has a passageway through the semipermeable wall connecting the beneficial drug formulation with the exterior of the delivery device.

An embodiment of the invention pertains to (1) a method of increasing the deliverability of a beneficial agent by formulating a heat-sensitive composition containing a beneficial agent and, (2) making the delivery system of the invention for increasing the deliverability of the beneficial agent. An embodiment of the invention pertains also to a method for administering a beneficial drug at a controlled rate to the rumen of a ruminant, which method comprises the steps of: (A) admitting into rumen a dispensing device comprising: (1) an outer wall formed of a semipermeable polymeric composition permeable to the passage of fluid and substantially impermeable to the passage of drug, the wall surrounding (2) an internal lumen containing a layer of a beneficial drug formulation comprising a dosage unit amount of drug for preforming a therapeutic program in a heat-sensitive pharmaceutically acceptable carrier that melts at body temperature and is a means for transporting the drug from the dispenser; (3) a gas-generating composition in the lumen, said gas-generating composition containing a density producing member for maintaining the dispenser in the rumen over a prolonged period of time; and, (4) passageway through the semipermeable wall communicating with the heat-sensitive drug formulation; (B) imbibing fluid through the semipermeable wall at a rate determined by the permeability of the semipermeable wall and the osmotic pressure gradient across the semipermeable wall causing gas-generating to produce gaseous carbon dioxide and continuously fill the lumen; (C) melting the drug formulation to form a flowable formulation; and, (D) delivering the beneficial drug formulation from the compartment by the gas continually exerting pressure against the melting drug formulation causing the drug formulation to be dispensed in a therapeutically effective amount through the passageway at a delivery system controlled rate to the rumen over a prolonged period of time.

Inasmuch as the foregoing specification comprises preferred embodiments of the invention, it is understood that variations and modifications may be made herein in accordance with the inventive principles disclosed without departing from the scope of the invention.

I claim:

1. A dispenser for delivering a beneficial agent formulation to an environment of use, the dispenser comprising:

(a) wall means for surrounding and forming an internal compartment;

(b) passageway means in the wall for connecting the internal compartment with the exterior of the dispenser;

(c) formulation means in the internal compartment comprising a beneficial agent formulation for absorbing thermal energy from the environment of use for making the beneficial agent formulation a deliverable formulation; and, (d) gas-generating means in the compartment for generating a gas in the presence of a fluid that passes through the wall means causing the gas-generating means to react and generate a gas that exerts pressure against the deliverable thermal energy sensitive formulation, thereby urging the deliverable formulation through the passageway means from the dispenser to the environment of use over time.

2. The dispenser for delivering a beneficial agent formulation to an environment of use according to claim 1, wherein the internal compartment comprises weight means for increasing the density of the dispenser for maintaining the dispenser in the environment of use during the beneficial agent formulation delivery period of time.

3. The dispenser for delivering a beneficial agent formulation to an environment of use according to claim 1, wherein the internal compartment comprises weight means possessing a density of at least 1.5 for increasing the density of the dispenser, thereby keeping the dispenser in the environment of use during the delivery period.

4. The dispenser for delivering a beneficial agent formulation to an environment of use according to claim 1, wherein the formulation means melts at a temperature of at least 25° C.

5. The dispenser for delivering a beneficial agent formulation to an environment of use according to claim 1, wherein the formulation means forms a fluid deliverable formulation at a temperature of at least 25° C.

6. The dispenser for delivering a beneficial agent formulation to an environment of use according to claim 1, wherein the formulation means forms a soft paste deliverable formulation at a temperature of at least 25° C.

7. The dispenser for delivering a beneficial agent formulation to an environment of use according to claim 1, wherein the beneficial agent formulation comprises a member selected from the group consisting of avermectin and ivermectin.

8. The dispenser for delivering a beneficial agent formulation to an environment of use according to claim 1, wherein the formulation means comprises a block copolymer of 1,2-butylene oxide and ethylene oxide.

9. The dispenser for delivering a beneficial agent formulation to an environment of use according to claim 1, wherein the wall means comprises an outer wall in laminar arrangement with an inner wall.

10. The dispenser for delivering a beneficial agent formulation to an environment of use according to claim 1, wherein the gas-generating means is mixed with an expandable means comprising a hydrogel for moving from a rested position to an expanded position for occupying an increasing area of the internal compartment and for cooperating with gas generated in the compartment for urging the beneficial agent formulation through the passageway over time.

11. The dispenser for delivering a beneficial agent formulation to an environment of use according to claim 1, wherein the gas-generating means is mixed with a member selected from the group consisting of iron, steel, iron magnesium alloy, and a mixture of cobalt and iron.

12. The dispenser for delivering a beneficial agent formulation to an environment of use according to claim 1, wherein the gas-generating means is mixed with a member selected from the group consisting of poly(ethylene oxide), poly(acrylamide), poly(hydroxyalkyl acrylate), poly(acrylic acid), and poly(saccharidel.

13. The dispenser for delivering a beneficial agent formulation to an environment of use according to claim 1, wherein the formulation means comprises a member selected from the group consisting of a block polymer of 1,2-butylene oxide and ethylene oxide, propylene glycol monostearate, propylene glycol distearate, triglyceride of saturated vegetable fatty acid, polyethylene glycol monostearate and a mixture of cocoa butter and beeswax, and food grade waxes.

14. The dispenser for delivering a beneficial agent formulation to an environment of use according to claim 1, wherein the formulation means is heat sensitive and the beneficial agent is a member selected from the group consisting of mebendazole, levamisole praziquantel, morantel, pirantel, avermectin, ivermectin, cephalosporin, sulfamethazine, sulfathiazole, dexamethazone and flumethazone.

15. The dispenser for delivering a beneficial agent formulation to an environment of use according to claim 1, wherein the wall means is formed of a member selected from the group consisting of a cellulose ester, cellulose diester, cellulose triester, cellulose ether, cellulose ester-ether, cellulose acylate, cellulose diacylate and cellulose triacylate.

16. The dispenser for delivering a beneficial agent formulation to an environment of use according to claim 1, wherein the wall means comprises a flux regulating agent selected from the group consisting of a polyhydric alcohol, polyalkylene glycol, polyalkylene diols, and a polyester of alkylene glycol.

17. The dispenser for delivering a beneficial agent formulation to an environment of use according to claim 1, wherein the wall means comprises a flux regulator selected from the group consisting of diethyl phthalate, dimethoxyethyl phthalate, dimethyl phthalate, triphenyl phthalate, citric acid esters, glycerol acetate esters, and butyl benzyl phthalate.

18. The dispenser for delivering a beneficial agent to an environment of use according to claim 1, wherein the gas-generating means comprises an acidic component and a basic component which when brought into fluid reactive contact generate a gas.

19. The dispenser for delivering a beneficial agent to an environment of use according to claim 1, wherein the gas-generating means comprises an acid selected from the group consisting of fumaric, tartaric, itaconic, maleic, citric, adipic, succinic, mesaconic and amino acids.

20. The dispenser for delivering a beneficial agent to an environment of use according to claim 1, wherein the gas-generating means comprises a member selected from the group consisting of sodium carbonate, potassium carbonate, calcium carbonate, magnesium carbonate, sodium bicarbonate, potassium bicarbonate, magnesium bicarbonate, and calcium bicarbonate.

21. A dispenser for delivering a beneficial agent formulation to an environment of use, the dispenser comprising:
(a) an inner body member having an internal lumen and provided with an opening for establishing communication with the lumen;
(b) an outer wall surrounding the inner body member, the outer wall comprising at least a part of a composition that is permeable to the passage of fluid;
(c) passageway means in the outer wall for communicating with the opening of the inner body member;
(d) a heat sensitive beneficial agent formulation in the lumen that forms a deliverable formulation at an environment of use temperature of at least 31° C.;
(e) first means in the lumen for expanding and increasing in size, said first means being adjacent to the heat sensitive formulation for pushing said formulation through the passageway means over time; and
(f) second means in the lumen for generating a gas for producing gaseous pressure and for cooperating with the first means for the heat sensitive formulation through the passageway over time.

22. The dispenser for delivering a beneficial agent formulation to an environment of use according to claim 21, wherein the dispenser comprises a third means in the lumen for increasing the density of the dispenser for maintaining the dispenser in the environment of use over time.

23. A delivery system for delivering a beneficial agent formulation to an environment of use, the delivery system comprising:
(a) a wall surrounding and forming an internal compartment, the wall comprising in at least a part a semipermeable composition permeable to the passage of fluid present in the environment of use and substantially impermeable to the passage of beneficial agent;
(b) a beneficial agent in the compartment, said beneficial agent being a member selected from the group consisting of antibloat, anthelmintic, antibiotic, anti-infectious and antiparasitic, antimicrobial, and antiflea beneficial agents;
(c) a passageway in the wall for connecting the internal compartment with the exterior of the delivery system for delivering the beneficial agent to the environment of use; and
(d) means in the compartment for generating a gas for filling the compartment thereby urging the beneficial agent through the passageway from the device, said gas-generating means mixed with a density member having a specific gravity greater than the specific gravity of a fluid present in the environment of use for keeping the delivery system in the environment of use over time.

24. The delivery system for delivering a beneficial agent formulation according to claim 23, wherein the gas-generating means is mixed with a hydrogel.

25. A method of administering to a ruminant a biologically active substance, said method comprising:
(a) admitting orally into the ruminant a dispenser, the dispenser comprising:
(1) a wall that surrounds and defines an internal lumen, the wall comprising a material permeable to the passage of fluid and substantially impermeable to the passage of biologically active substance;
(2) first means in the lumen for containing a biologically active substance, said means a heat responsive composition that absorbs heat from the ruminant and thereby forms a dispensable composition for administering the biologically active substance;
(3) a passageway in the dispenser communicating with the lumen for administering the biologically active substance from the dispenser;
(4) second means in the lumen for generating a gas in the presence of fluid imbibed into the lumen for producing gaseous pressure against the first means for urging is from the lumen;
(5) third means in the lumen for maintaining the dispenser in the ruminant over time, said third means having a density greater than the density of a fluid present in the rumen of a ruminant; and
(6) administering the biologically active substance by the means containing the biologically active substance absorbing heat and the means for generating gas producing a gas, whereby through the combined operations the beneficial substance is delivered.

26. The method of administering to a ruminant a bioliogically active substance according to claim 25, wherein the passageway comprises at least one pore.

27. The method of administering to a ruminant a biologically active substance according to claim 25, wherein the passageway comprises a porous polymer composition comprising more than one micropore.

28. The method of administering to a ruminant a biologically active substance according to claim 25, wherein passageway is formed by leaching a pore forming material from the wall.

29. The method of administering to a ruminant a biologically active substance according to claim 25, wherein the active substance is avermectin.

30. The method of administering to a ruminant a biologically active substance according to claim 25, wherein the active substance is ivermectin.

* * * * *